(12) United States Patent
Anderskewitz et al.

(10) Patent No.: US 6,197,753 B1
(45) Date of Patent: Mar. 6, 2001

(54) PYRANOSIDE DERIVATIVES

(75) Inventors: Ralf Anderskewitz, Bingen; Kurt Schromm, Ingelheim am Rhein; Ernst-Otto Renth, Kiel; Franz Birke, Ingelheim am Rhein; Hans M. Jennewein, Wiesbaden; Christopher J. M. Meade, Bingen; Andreas Ding, Biberach, all of (DE)

(73) Assignee: Boehringer Ingelheim KG, Ingelheim (DE)

( * ) Notice: Subject to any disclaimer, the term of this patent is extended or adjusted under 35 U.S.C. 154(b) by 0 days.

(21) Appl. No.: 09/264,649

(22) Filed: Mar. 8, 1999

Related U.S. Application Data

(63) Continuation-in-part of application No. PCT/EP97/04948, filed on Sep. 10, 1997.

(51) Int. Cl.$^7$ .......... A61K 31/70; A01N 43/04; A01N 37/10
(52) U.S. Cl. .......... 514/23; 514/532; 514/546
(58) Field of Search .......... 514/23, 532, 546

(56) References Cited

U.S. PATENT DOCUMENTS 5,246,965 * 9/1993 Main .......... 514/532

OTHER PUBLICATIONS

F.C. Barone et al., Time–Related Changes in Myeloperoxidas Activity and Leukotriene B4 Receptor Binding Reflect Leukocyte Influx in Cerebral Focal Stroke, Mol. Chem. Neuropathology 1995, 24:13–30 [Barone et al.].

J. Britton, Dietary Fish Oil and Airways Obstruction, Thorax 1995, 50 (Suppl. 1): 511–515 [Britton].

U. Costabel et al., Local Immune Components in Chronic Obstructive Pulmonary Disease, Respiration 1992, 59(Suppl. 1): 17–19 [Costabel et al.].

K. Schlosser et al., Increased Leukotriene B4 Snythesis in Polymorphonuclear Leukocytes of Smokers, Klin Wochenschr 1988, 66 (Suppl. XI): 120–124 [Schlosser et al.].

W.H. Thornton, Jr. et al., Leukotriene B4 is Measurable in Serum of Smokers and Nonsmokers, Clin. Chem. 1989, 35/3: 459–460 [Thornton et al.].

A.B. Thompson, Intraluminal Airway Inflammation in Chronic Bronchitis, Am. Rev. Respir. Dis. 1989, 140:1527–1537 [Thompson et al.].

D. Stanescu et al., Airway Obstruction, Chronic Expectoration, and Rapid Decline of FEV1 in Smokers are Associated with Increased Levels of Sputum Neutrophils, Thorax 1996, 51:267–271 [Stanescu et al.].

English language translation of WO 97/21670 and WO 93/16036.

* cited by examiner

*Primary Examiner*—James O. Wilson
*Assistant Examiner*—Howard Owens
(74) *Attorney, Agent, or Firm*—Robert P. Raymond; Alan R. Stempel; Timothy X. Witkowski

(57) ABSTRACT

Pyranoside derivatives of the formula I wherein 1, m and n independently of one another denote an integer chosen from 0, 1, 2, 3 and 4 and $1+m+n \leq 4$. These are are $LTB_4$-antagonists. Also disclosed are processes for making these compounds.

13 Claims, No Drawings

PYRANOSIDE DERIVATIVES

RELATED APPLICATIONS

This application is a continuation-in-part of International Application PCT/EP97/04948 filed on Sep. 10, 1997. Benefit of the earlier filing date of the prior International Application is hereby claimed, pursuant to 35 U.S.C. 365(c) and 120.

DESCRIPTION OF THE INVENTION

The present invention relates to new pyranoside derivatives, processes for preparing them and their use in pharmaceutical compositions. The new pyranoside derivatives correspond to general formula I

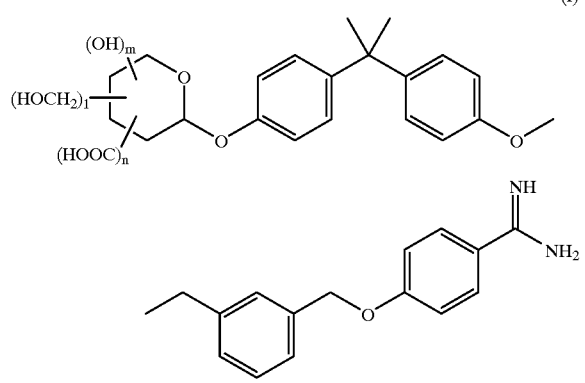

wherein
1, m and n independently of one another denote an integer chosen from 0, 1, 2, 3 and 4 and 1+m+n<4
in the form of their racemates, in enantiomerically pure or concentrated form, optionally as pairs of diastereomers and are obtained in the form of free bases or salts, preferably with physiologically acceptable acids.

The compounds according to the invention are potent $LTB_4$-antagonists. In particular the compound of Example 1 is obtained in vivo as a metabolite of an $LTB_4$-antagonistic compound and in the receptor binding test it has a $K_i$-value of 1.0 nM.

As has been found, the compounds of formula I are characterised by their versatility of use in the therapeutic field. Particular mention should be made of those applications in which the $LTB_4$-receptor-antagonistic properties play a part. Examples include, in particular: arthritis, asthma, chronic obstructive lung diseases, such as chronic bronchitis, psoriasis, ulcerative colitis, gastropathy or enteropathy induced by nonsteroidal antiinflammatories, cystic fibrosis, Alzheimer's disease, shock, reperfusion damage/ischaemia, atherosclerosis and multiple sclerosis.

The new compounds may also be used to treat diseases or conditions in which the passage of cells from the blood through the vascular endothelium into the tissues is of importance (such as metastasis) or diseases and conditions in which the combination of $LTB_4$ or another molecule (such as 12-HETE) with the $LTB_4$-receptor influences cell proliferation (such as chronic myeloid leukaemia).

The new compounds may also be used in combination with other active substances, e.g. those which are used for the same indications, or for example with antiallergics, secretolytics, 12-adrenergics, inhaled steroids, antihistamines and/or PAF-antagonists. They may be administered by topical, oral, transdermal, nasal or parenteral route or by inhalation.

The activity ratios may be investigated pharmacologically and biochemically using tests such as those described in WO 93/16036, pp. 15 to 17 —the contents of which are referred to herein.

The therapeutic or prophylactic dose depends not only on the potency of the individual compounds and the body weight of the patient but also on the nature and gravity of the illness. For oral administration the dose is between 10 and 500 mg, preferably between 20 and 250 mg. For inhalation the patient is given between about 0,5 and 25 mg, preferably between about 2 and 20 mg of active substance.

Inhalable solutions generally contain between about 0.5 and 5% of active substance. The new compounds may be administered in conventional preparations, e.g. as plain or coated tablets, capsules, lozenges, powders, granules, solutions, emulsions, syrups, inhalable aerosols, ointments or suppositories.

The Examples which follow show some possible ways of formulating the preparations:

Formulation examples

| 1. Tablets Composition: | |
| --- | --- |
| Active substance according to invention | 20 parts by weight |
| Stearic acid | 6 parts by weight |
| Glucose | 474 parts by weight |

The ingredients are processed in the usual way to form tablets weighing 500 mg. If desired the content of active substance may be increased or reduced and the quantity of glucose reduced or increased accordingly.

| 2. Suppositories Composition: | |
| --- | --- |
| Active substance according to invention | 100 parts by weight |
| Lactose, powdered | 45 parts by weight |
| Cocoa butter | 1555 parts by weight |

The ingredients are processed in the usual way to form suppositories weighing 1.7 g.

3. Powder for Inhalation

Micronised active substance powder (compound of formula I; particle size about 0.5 to 7 μm) is packed into hard gelatin capsules in a quantity of 5 mg, optionally with the addition of micronised lactose. The powder is inhaled from conventional inhalers, e.g. according to DE-A 33 45 722, which is referred to herein.

The compounds according to the invention are prepared by methods which are known per se from the prior art. Thus, the compounds of general formula I

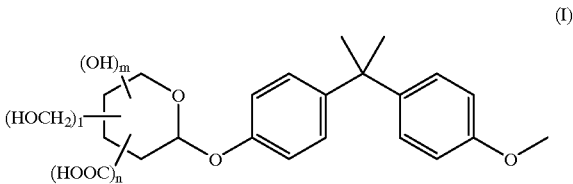

-continued

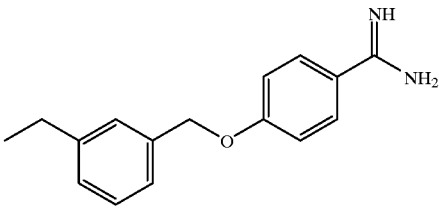

wherein 1, m and n are as hereinbefore defined, are prepared by reacting 4-[[3-[[4-[1-(4-hydroxyphenyl)-1-methylethyl] phenoxy]methyl]phenyl]methoxy]-benzenecarboximidamide with a glucose derivative of general formula II

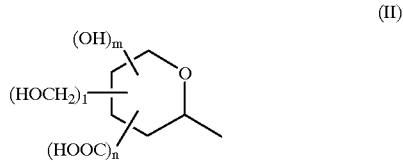

wherein when n>0 the carboxyl group is optionally protected in the form of a $C_{1-4}$-alkyl ester and the hydroxy groups are protected in the form of acyl groups of an aliphatic or aromatic carboxylic acid and X denotes a leaving group which may be displaced by a phenoxide oxygen, converted from a phenoxide and optionally the ester groups are saponified.

The compounds according to the invention may also be prepared from an optionally protected glucose derivative (II) and the abovementioned phenol using basic heavy metal compounds such as $Ag_2O$ or $CdCO_3$ in inert solvents such as toluene or dichloromethane. The product is optionally freed of the protecting groups by saponification.

The compounds (I) may also be prepared from derivatives of formula (II) and the abovementioned phenol using Lewis acids such as, for example, $BF_3$, $AlCl_3$, $ZnCl_2$, $SnCl_4$, $TiCl_4$, or from alkoxide derivatives of these Lewis acids in inert solvents such as toluene, dichloromethane, etc.

Furthermore, the compounds according to the invention may be prepared from an optionally protected derivative (II) wherein X=OH and the abovementioned phenol using acid catalysts such as e.g. methanesulphonic acid or tetrafluoroboric acid or using Lewis acids such as for example $BF_3$, $AlCl_3$, $ZnCl_2$, $SnCl_4$, $TiCl_4$, or from alkoxide derivatives of these Lewis acids in inert solvents such as aliphatic, aromatic, alkylsubstituted aromatics or in a halogenated hydrocarbon—preferably in toluene or in dichloromethane.

$C_{1-4}$-alkyl in the preparation processes described above generally represents a branched or unbranched hydrocarbon group having 1 to 4 carbon atoms, which may optionally be substituted with one or more halogen atoms—preferably fluorine—, which may be identical to or different from one another. Examples include the following hydrocarbon groups: methyl, ethyl, propyl, 1-methylethyl (isopropyl), n-butyl, 1-methylpropyl, 2-methylpropyl and 1,1-dimethylethyl.

The compounds according to the invention may be prepared starting from compounds which are known from the prior art, using inter alia the methods described in the following Examples. Various other embodiments of the processes will become apparent to the skilled person from the description provided. However, it is expressly pointed out that these Examples and the associated description are provided solely for illustration and must not be regarded as limiting the invention.

EXAMPLES

Example 1

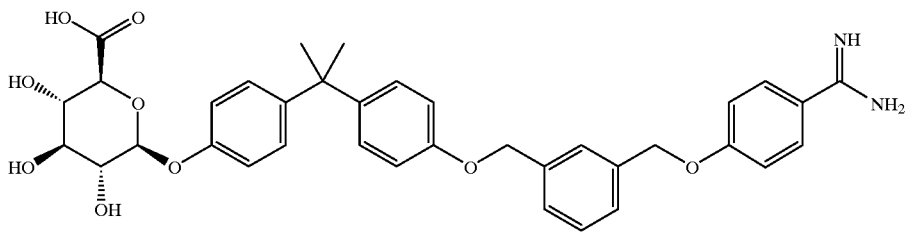

4-[[3-[[4-[1-(4-hydroxyphenyl)-1-methylethyl]phenoxy] methyl]phenyl]methoxy]-benzenecarboximidamide-O-gluctironide To a solution of 37.8 g of 4-[[3-[[4-[1-(4-hydroxyphenyl)-1-methylethyl]phenoxy]methyl]phenyl]methoxy]-benzenecarboximidamide in 1000 ml dimethoxyethane is added a 30% solution of sodium methoxide in methanol and the mixture is stirred for 10 min. After cooling to −10° C., 32.4 g of methyl acetobromo-α-D-glucuronate are added and the mixture is stirred for 48 h at ambient temperature. After the addition of a solution of 3.5 g of LiOH in 100 ml of water the mixture is stirred for a further 48 h and the solvent is distilled off at ambient temperature in cacao. The residue is dissolved in 200 ml of eluant $H^1$) and the aqueous phase precipitated is separated off. The substance is chromatographed using preparative thin-layer plates, isolated after extraction with methanol and crystallised with water. Yield: 5.3 g (Mp. 205° C. (decomp.)).

[1])36 parts of n-butanol, 15 parts of formic acid, 15 parts of water, 15 parts of acetone, 5 parts of chloroform are combined, shaken thoroughly, and after 3 days the aqueous phase precipitated is separated off.

Example 2

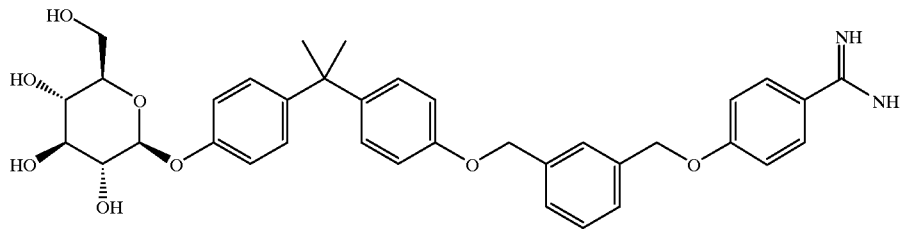

4-[[3-[[4-[1-(4-hydroxyphenyl)-1-methylethyl]phenoxy] methyl]phenyl]methoxy]-benzenecarboximidamide-O-glucose The compound is prepared according to the method of Example 1 from 4-[[3-[[4-[1-(4-hydroxyphenyl)-1-methylethyl]phenoxy]methyl]phenyl]methoxy]-benzenecarboximidamide and tetraacetylbromoglucose.

What is claimed is:

1. A compound of the formula I

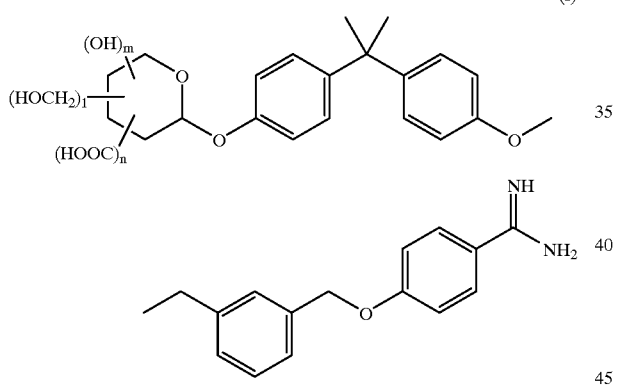
(I)

wherein 1, m and n independently of one another denote an integer chosen from 0, 1, 2, 3 or 4, and $1+m+n \leq 4$, or a pharmaceutically acceptable salt thereof.

2. 4-[[3-[[4-[1-(4-hydroxyphenyl)- 1-methylethyl] phenoxy]methyl]-phenyl]methoxy]-benzenecarboximidamide-O-glucuronide.

3. 4-[[3-[[4-[1-(4-hydroxyphenyl)-1-methylethyl] phenoxy]methyl]-phenyl]methoxy]-benzenecarboximidamide-O-glucose.

4. A process for preparing a compound of the formula I

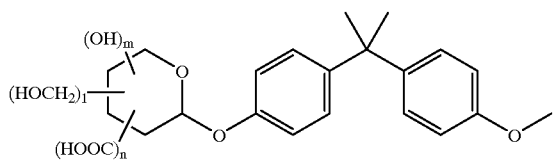
(I)

-continued

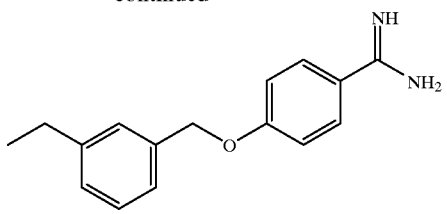

wherein 1, m and n independently of one another denote an integer chosen from 0, 1, 2, 3 or 4, and $1+m+n \leq 4$, wherein 4-[[3-[[4-[1-(4-hydroxyphenyl)-1-methylethyl]phenoxy] methyl]phenyl]methoxy]-benzenecarboximidamide is reacted with a glucose derivative of the formula II

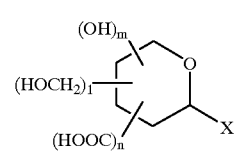
(II)

wherein, if n>0, the carboxyl group may optionally be in the form of a $C_{1-4}$-alkylester and the hydroxyl groups in the form of acyl groups are protected with an aliphatic or aromatic carboxylic acid and X denotes a leaving group which may be displaced by a phenoxide oxygen, and optionally the ester groups are saponified.

5. The process of claim 4, wherein the reaction is carried out in the presence of an acidic catalyst or a Lewis acid.

6. The process of claim 5, wherein the acidic catalyst is methanesulphonic acid or tetrafluoroboric acid.

7. The process of claim 5, wherein the Leuwis acid is selected from the group consisting of $BF_3$, $AlCl_3$, $ZnCl_2$, $SnCl_4$ and $TiCl_4$ or is an alkoxide of a Lewis acid selected from this group.

8. The process of claim 4, wherein the reaction is carried out in the presence of a transition metal compound that is a basic catalyst.

9. The process of claim 8, wherein the transition metal compound is $Ag_2O$ or $CdCO_3$.

10. The process of claim 4, 5, 6, 7, 8 or 9, wherein an aliphatic or aromatic hydrocarbon, an alkyl-substituted aromatic or a halogenated hydrocarbon is used as the reaction medium.

11. The process of claim 10 wherein toluene or dichloromethane is used as solvent.

12. A pharmaceutical composition comprising a compound of formula I, in accordance with claim 1, 2 or 3, and a pharmaceutically acceptable carrier.

13. A method for the treatment of arthritis, asthma, chronic obstructive lung disease, psoriasis, ulcerative colitis, gastropathy or enteropathy induced by nonsteroidal antiinflammatories, cystic fibrosis, reperfusion damage/ischaemia, or atherosclerosis, the method comprising administering, to a host suffering from such condition, a therapeutically acceptable amount of a compound of the formula I, in accordance with claim 1, 2, or 3.

* * * * *

UNITED STATES PATENT AND TRADEMARK OFFICE
CERTIFICATE OF CORRECTION

PATENT NO.    : 6,197,753 B1
DATED         : March 6, 2001
INVENTOR(S)   : Anderskewitz, Ralf; Schromm, Kurt; Renth, Ernst-Otto; Birke, Franz; Jennewein, Hans M.; Meade, Christopher J.M.; and Ding, Andreas It is certified that error appears in the above-identified patent and that said Letters Patent is hereby corrected as shown below:

Title page,
OTHER PUBLICATIONS,
Line 10, "Snythesis" should read -- Synthesis --.

ABSTRACT,
Line 3, following the chemical formula, delete the duplicate word "are".

Column 4,
Line 2, "Lcwis" should read -- Lewis --.

Column 6,
Line 53, "Leuwis" should read -- Lewis --.

Signed and Sealed this

Twenty-third Day of July, 2002

*Attest:*

JAMES E. ROGAN
*Director of the United States Patent and Trademark Office*

*Attesting Officer*